United States Patent [19]

Stoermer, III et al.

[11] Patent Number: 4,976,931
[45] Date of Patent: * Dec. 11, 1990

[54] GENERATION OF ANAEROBIC OR MICROAEROPHILIC ATMOSPHERE

[75] Inventors: Ralph T. Stoermer, III, York County, Pa.; James C. Darner, San Jose, Calif.

[73] Assignee: Becton, Dickinson and Company, Franklin Lakes, N.J.

[*] Notice: The portion of the term of this patent subsequent to Dec. 31, 2002 has been disclaimed.

[21] Appl. No.: 808,223

[22] Filed: Dec. 12, 1985

Related U.S. Application Data

[63] Continuation-in-part of Ser. No. 584,174, Feb. 27, 1984, Pat. No. 4,562,051.

[51] Int. Cl.$^5$ ............................................... B01J 8/02
[52] U.S. Cl. ..................................... 422/211; 48/192; 422/86; 422/212; 422/236; 422/238; 422/239; 422/219; 435/287; 435/807
[58] Field of Search ................ 422/86, 211, 222, 236, 422/238, 239; 423/219; 48/192; 435/287, 801

[56] References Cited

U.S. PATENT DOCUMENTS

| 3,246,959 | 4/1966 | Brewer | 435/801 |
| 3,483,089 | 12/1969 | Brewer | 435/801 |
| 4,012,203 | 3/1977 | Rosiere | 23/282 |
| 4,013,422 | 5/1977 | Spinner et al. | 23/282 |
| 4,023,934 | 5/1977 | Spinner et al. | 23/254 R |
| 4,038,148 | 7/1977 | Miller et al. | 195/127 |
| 4,078,893 | 3/1978 | Gilman et al. | 23/253 TP |
| 4,200,610 | 4/1980 | Swaine et al. | 422/239 |
| 4,287,306 | 9/1981 | Brewer | 435/287 |
| 4,289,855 | 9/1981 | Whitley | 435/287 |
| 4,347,222 | 8/1982 | Beall et al. | 422/211 |
| 4,377,554 | 3/1983 | Johnson | 422/239 |
| 4,428,907 | 1/1984 | Heijenga et al. | 422/61 |
| 4,562,051 | 12/1985 | Stoermer, III et al. | 423/219 |

Primary Examiner—Robert J. Warden
Assistant Examiner—Timothy M. McMahon
Attorney, Agent, or Firm—Richard E. Brown

[57] ABSTRACT

Apparatus and method for generating an anaerobic or microaerophlic atmosphere. A package consisting of a foil envelope has internal compartments for a hydrogen generating material, for a catalyst and for receiving water. The catalyst compartment is provided with a flash arrestor. Water, on being added to the envelope, reacts with the hydrogen generating material. The liberated hydrogen then reacts catalytically with oxygen in the atmosphere external to the package.

20 Claims, 7 Drawing Sheets

GENERATION OF ANAEROBIC OR MICROAEROPHILIC ATMOSPHERE

The present application is a Continuation-in-part of U.S. Pat. application Ser. No. 584,174, filed Feb. 27, 1984, now U.S. Pat. No. 4,562,051.

FIELD OF THE INVENTION

The present invention relates generally to an apparatus and method for the generation of an anaerobic or microaerophilic atmosphere which is conducive to the growth of certain microorganisms.

DESCRIPTION OF THE PRIOR ART

It is well known that some microorganisms require an aerobic atmosphere for growth, others require an anaerobic atmosphere, and still others require a microaerophilic atmosphere in which the oxygen level is between aerobic and anaerobic. In addition, some microorganisms require specific levels of carbon dioxide for growth.

The attainment of an aerobic atmosphere is relatively simple, in most cases merely requiring aeration of the culture media. Anaerobic conditions are more difficult to attain and the prior art contains many devices and processes for producing anaerobic atmosphere. U.S. Pat. No. 3,246,969, to Brewer discloses a device for generating such anaerobic atmosphere by generation of hydrogen for reaction with oxygen in the atmosphere of an anaerobic apparatus such as that disclosed in U.S. Pat. No. 3,483,089 to Brewer. The reaction between the hydrogen and oxygen is catalyzed by a platinum catalyst in the anaerobic apparatus.

U.S. Pat. No. 4,347,222 to Beall discloses disposition of the catalyst in one receptacle of a unitary apparatus. This apparatus requires means for puncturing seals between several of the receptacles. The puncture means is supplied by a device which is separate from the gas generating apparatus or as part of a mated container.

The reaction between hydrogen and oxygen in the presence of a catalyst is strongly exothermic. Flashing, and even explosion, can occur at the catalyst surface, particularly if the catalyst is finely divided and no means are provided to dissipate the heat generated.

U.S. Pat. No. 4,013,422 to Spinner discloses a container having a material for generating a reducing gas, such as hydrogen, for reaction, in the presence of a catalyst, with oxygen. The Spinner apparatus, however, uses an exposed catalyst pellet with no provision for heat removal. In addition, it relies on the breaking of an ampoule containing a liquid and thereby instantaneous release of the liquid into contact with the material for generating the reducing gas. Thus no means is provided for controlling the rate at which the contact is made. Experience has shown that contact at a slow and controlled rate is essential for accurate attainment of pre-determined final oxygen levels, particularly in those cases where it is desired to reduce, but not eliminate, the oxygen in the atmosphere.

U.S. Pat. No. 4,287,306 to Brewer describes a further apparatus for generating anaerobic atmospheres. In accordance with this patent, a flexible sealed package is provided with a catalyst coated onto the exterior surface of the package for use in catalyzing the reaction between oxygen outside the package and hydrogen generated within the package. This apparatus, like the Spinner apparatus, has the disadvantage of exposed active catalyst.

U.S. Pat. No. 4,289,855 to Whitley discloses a safety catalyst package designed to reduce the danger of flashing or explosion. The Whitley package encloses a catalyst within holes and folds in a metal foil net. The net, which is inside of a container having holes for gas exchange, is composed of a heat conducting material, and thereby functions to remove heat from the catalyst vicinity. The Whitley disclosure is of a safety catalyst package only, and makes no provision for supply of hydrogen.

A package, for use in an anaerobic jar and specifically designed for attainment of a microaerophilic atmosphere, is disclosed in U.S. Pat. No. 4,377,554 to Johnson. The Johnson invention relies on control of "wetover" and "condensation" times for successful generation of microaerophilic atmospheres, and uses conventional exposed catalysts attached either to the outside of the package or to the lid of the jar.

A cardboard package for use in generating an anaerobic atmosphere is commercially available from the BBL Microbiology Systems Division of Becton Dickinson Company. This package includes a catalyst chamber mounted in the side of he box. The catalyst chamber is porous on both sides to permit generated hydrogen to flow through the chamber and thus react with the catalyst.

SUMMARY OF THE INVENTION

In accordance with one embodiment of the present invention, there is provided a package for removing all or part of the oxygen in a gaseous mixture. The package includes a metallic foil envelope having a plurality of internal compartments. One compartment contains a material to generate hydrogen upon reaction with water. Another compartment contains a material to catalyze the reaction between the hydrogen and oxygen. Another compartment is adapted to receive water.

In one embodiment, the catalyst containing compartment has at least one opening in its outside wall to provide gas communication between the compartment and the atmosphere external to the envelope. A layer of porous thermostable material is positioned over the holes on the inside of the catalyst containing compartment. The catalyst containing compartment is additionally provided with a sealed over on the inside of the compartment to separate the compartment from the inside of the envelope.

The water receiving compartment is positioned over the catalyst containing compartment so that, when the frangible seal has been broken and water has been added, the water is above the catalyst and separated therefrom by the sealed cover. The water thus serves as a heat sink to conduct heat away from the catalyst during use.

The water receiving and hydrogen generating compartments are in fluid communication through a channel provided with fluid transfer means. The fluid transfer means may be a wick prepared from any suitable material chosen such that the water passes from the water receiving compartment into the hydrogen generating compartment at a pre-determined rate.

In accordance with another aspect of the present invention, there is provided a carbon dioxide generating composition formulated in a manner to generate carbon dioxide and provide an acidic pH whereby, when used in a gas generating package along with a hydrogen generator, acidic to neutral pH conditions are maintained to prevent carbon dioxide absorption which may occur under alkaline conditions.

In accordance with another aspect of the invention, there are provided one or more indicators attached to the outside of the foil package which show oxygen and carbon dioxide levels in the atmosphere.

In accordance with another aspect of the invention, an independent catalyst compartment is provided which is not associated or in combination in the same package with gas generating means.

Thus it is an object of the invention to provide a unitary package for removal of oxygen from a gaseous atmosphere by providing materials within the package which, on contact with water, will produce hydrogen to react catalytically with the oxygen. It is a further object to provide the catalyst in a compartment of the package. It is a still further object to improve safety by providing the catalyst with a flash arrestor.

DETAILED DESCRIPTION OF THE INVENTION

Figure 1:
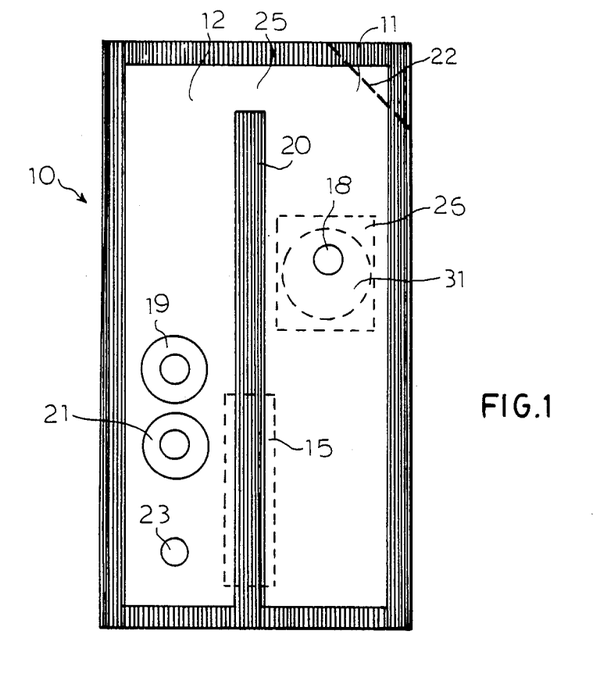
FIG. 1 is a top view of the package of the invention.
Figure 2:
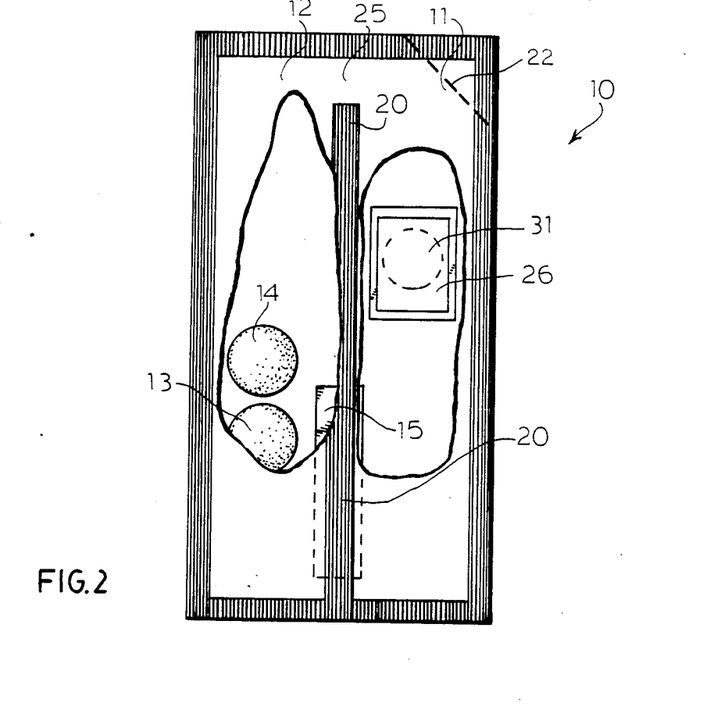
FIG. 2 is a top view of the package of the invention with portions of the top panels of the foil envelope removed.
Figure 3:
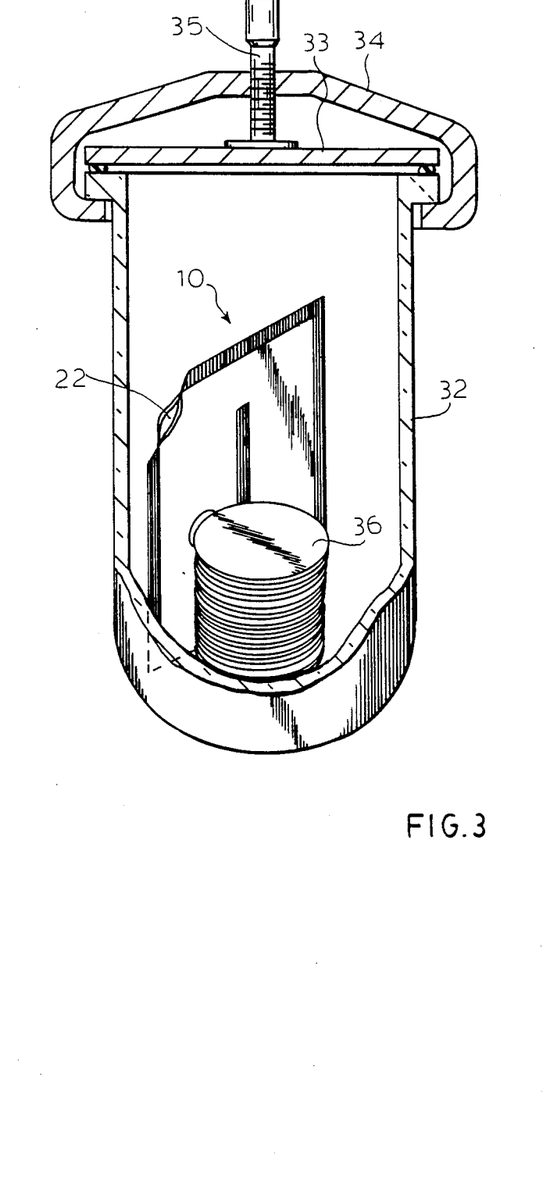
FIG. 3 is a perspective view, partially broken away, of an anaerobic jar showing the use of the gas generating package of FIG. 1 and FIG. 2 of the invention.

Referring now to FIG. 1 and 2, there is shown a device for removing a pre-determining amount of oxygen from a gaseous atmosphere comprising a package in the form of an envelope 10. Envelope 10 is made of a suitable material which is impervious to the atmosphere and moisture, and which is inert to materials contained within the package and gases generated therein and which is not destroyed by the heat of reaction released during use of the package, as hereinafter described. Thus, for example, the envelope 10 may be formed of a metallic foil, such as aluminum, which may be coated on its inner surface with a thermoplastic material, such as polyethylene or a polymer formed of vinyl chloride. The envelope 10 may be formed from two panels suitably secured together around the edges by heat sealing. In use, as shown as FIG. 3, the envelope 10 is placed into container 32 having a lid 33 which forms a gas tight seal when the bracket 34 is tightened by the screw 35. Petri dishes 36 containing plated culture media requiring a predetermined level of oxygen in the atmosphere are also placed in the container 32 prior to sealing the container. The closed container has a known volume of air and hence a known volume of oxygen. The volume of the package and a given number of petri dishes is also known and is accounted for in calculating the stoichiometric amount of hydrogen generating material required to reduce the atmosphere to the predetermined level of oxygen.

The interior of the envelope is divided into a first gas generating compartment 12 and a second liquid-receiving compartment 11 by a suitable partition 20 which is formed, for example, by heat sealing when the top and bottom panels of the envelope are joined. The compartment 12 includes gas generating material in the form of a tablet 13, which includes materials capable of generating hydrogen and, optionally a tablet 14, which includes materials capable of generating carbon dioxide. In general, the hydrogen generating material is used in when an anaerobic atmosphere is desired. When sodium borohydride is used as the hydrogen generating material, about 0.9 gm is used to provide an anaerobic atmosphere in a 2.5 liter container. When sodium borohydride is used to generate a microaerophilic atmosphere in a 2.5 liter container, about 0.15 to about 0.4 gm, preferably from about 0.20 gm to about 0.35 gm is used to remove from about 20 to about 80 percent of the oxygen present.

The interior compartments 11 and 12 are in internal fluid and gas flow communication with each other through a channel in the portion 20 at the bottom of the envelope. For purposes of discussion, the top of the envelope is considered to be that end of the envelope wherein water in introduced. The bottom of the envelope is the other end. Preferably, the channel is provided with controlled transfer means, such as the use of a wick 15 (shown in phantom outline in FIG. 1 and FIG. 2). The wick 15 is capable of permitting both liquid flow between compartments 11 and 12 at a controlled rate as described in U.S. Pat. No. 4,377,554, the subject matter of which is incorporated herein by reference. The wick 15 extends through the partition 20 into each of the compartments 11 and 12. As a result of the porosity of the wick, liquid diffuses between the internal compartments. Suitable, porous materials for use as wick 15 are filter paper, blotting paper, cotton twill, etc. A preferred wick material is filter paper having the designation Whatman #4. It should be understood that although the wick is shown as being a single sheet, it may be divided into two or more sheets. As particularly shown, the partition 20 terminates before the top of the package whereby the compartments are in communication with each other through gap 25 above the partition. The package is designed to be used in a manner such that liquid introduced into compartment 11 does not reach gap 25 whereby only gas flow communication between compartments 11 and 12 occurs through gap 25 at the top of the envelope.

Figures 4, 5, 6, 7:
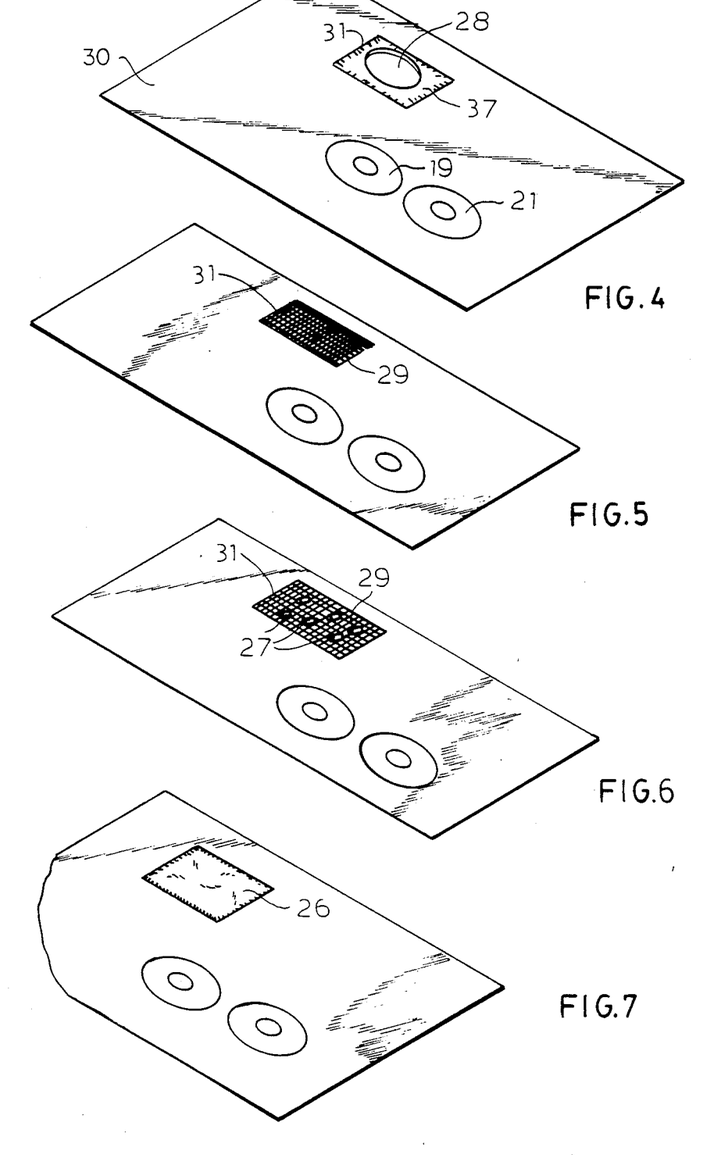
FIGS. 4-7 illustrate various steps in forming one embodiment of the catalyst compartment of the package of FIG. 1 in accordance with the invention.

In accordance with one embodiment of the present invention as shown in FIGS. 4-7, a separate catalyst compartment 31 is provided within envelope 10. For purposes of discussion, the panel in which the catalyst compartment is formed will be referred to as the "bottom" panel. The other panel which is mated with and sealed to the bottom panel to complete formation of the envelope, is referred to as the "top" panel. FIG. 4 shows compartment 31 which may be any shape, formed as a cavity in bottom panel 30 of envelope 10. The portion, 32, of bottom panel 30 which forms the outside wall of the compartment 31 is cut to provide at least one hole 28 therein, leaving a residual flange portion 37 in the bottom of the cavity. For added structural integrity a plurality of smaller holes may be used. Hole 28 provides gas communication between catalyst 27 and the atmosphere external to envelope 10. As shown in FIG. 5, a flash arrestor 29 is then secured to the flange 3 over hole 28 by any suitable means, such as by gluing the flash arrestor in place. Flash arrestor 29 may be of any suitable thermostable, porous material, such as fiberglass cloth, perforated metal foil or metal screening. The mesh size of flash arrestor 29 is preferably from about 100 to 300 American Standard Sieve Size, most preferably from about 180 to 220.

Catalyst 27 is then placed in compartment 31 above flash arrestor 29. Although catalyst 27 is particularly shown in FIG. 6 as pellets, other forms of catalyst may be used, as, for example, spheres, cylinders, powders, strips and the like. The catalyst may be used as such, or it may be supported on an inert carrier such as alumina, carbon, fiberglass cloth, synthetic polymer and glass tape. A variety of materials may be used as the catalyst, such as platinum, rhodium, ruthenium, iridium or, preferably, palladium.

Compartment 31 is then sealed on the internal side the bottom panel 30 by attachment of cover 26. Cover 26 is prepared from a suitable material, such as metallic foil and is sealed around its edge to bottom panel 30. Cover 26 thereby protects catalyst 27 from contact with water in water receiving compartment 11. The water, after being added to water receiving compartment 11 is positioned adjacent to the catalyst and serves as a heat sink to remove heat from catalyst 27.

A second cover (not shown) is placed over hole 28 on the outside of bottom panel 30 to protect the catalyst from ambient moisture when the envelope is used. The second cover is prepared from a suitable material, such as metallic foil and is releasably sealed around its edge to bottom panel 30. The second cover is preferably provided with a grasping portion so that the cover is easily grasped and removed by the user just before or after addition of water to water receiving compartment 11.

Figure 8:
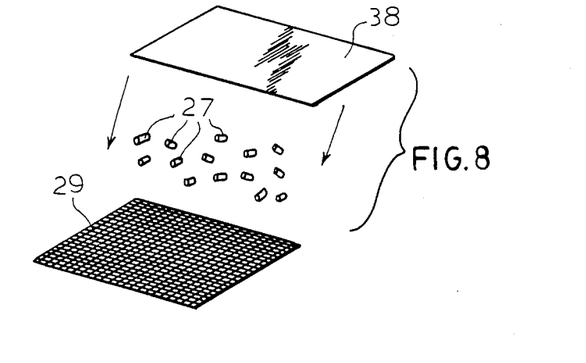
FIGS. 8 and 9 illustrate steps in forming a separate catalyst unit in accordance with the invention.
Figure 9:
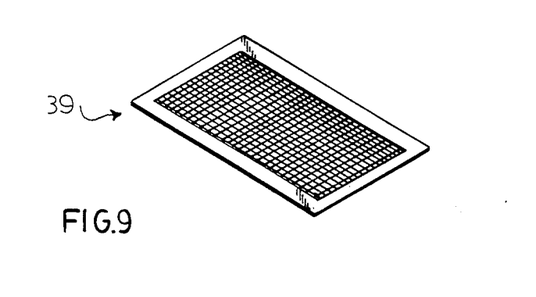
Figure 10:
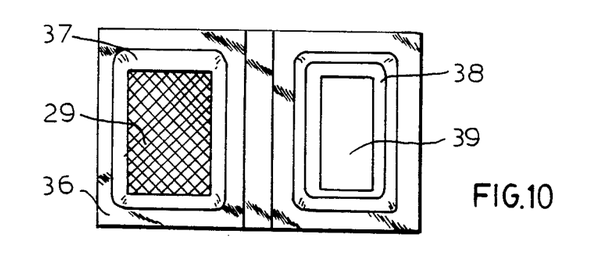
FIGS. 10-16 illustrate various steps in forming and utilizing a separate catalyst unit in accordance with a further embodiment of the invention.
Figure 17:
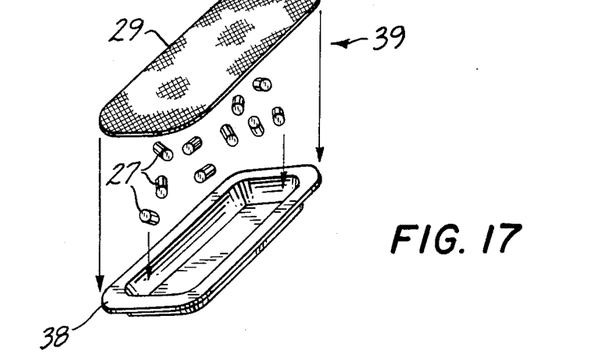
FIG. 17 illustrates a further embodiment of the catalyst unit of FIGS. 8 and 9.

A further embodiment of the invention is shown in FIGS. 8, 9 and 17. In this embodiment, a unitary piece of flame arrestor 29 is mated with a backing material 38 in a manner so as to enclose a suitable amount of catalyst 27 and provide a catalyst unit 39. The backing material is prepared from a suitable material, such as metal foil, and is sealed around the edge of the flame arrestor 29 to provide the catalyst unit 39. As shown in FIG. 17, the backing material 38 may be formed into a receptacle with a flanged edge for receiving the catalyst pellets and for subsequent sealing attachment of the flame arrestor 29.

The catalyst unit 39 may be placed in the catalyst compartment 31 in the same manner heretofore described for the loose catalyst. Alternatively, the backing material 38 of the catalyst unit 39 can be adhered to the outside of the bottom panel 30 or the top panel of the envelope or can be adhered to the inside wall 32 of the anaerobic jar shown in FIG. 3.

Figure 18:
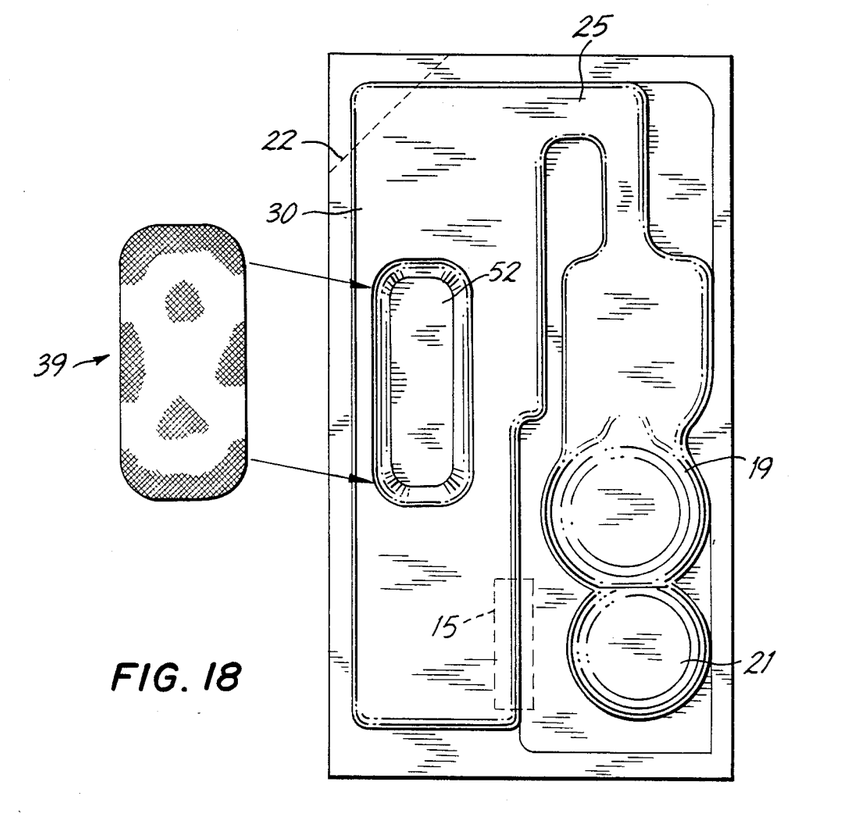
FIG. 18 illustrates the use of the catalyst unit of FIG. 17 with a further embodiment of a catalyst package.

In a further embodiment of the catalyst package of this invention, as shown in FIG. 18, a cavity 52 is formed in the outside of bottom panel 30 for receiving the catalyst unit 39 of FIG. 17. The cavity 52 is preferably sized to receive the catalyst unit 39 so that the flame arrestor 29 is substantially flush with the surface of bottom panel 30. The catalyst unit 39 is adhered to the bottom panel 30 by any suitable adhesive or means. Of course, for this embodiment the hole 28 is not required in bottom panel 30.

A further embodiment of the invention is shown in FIGS. 10-16. In this embodiment a panel 54 of suitable material, such as metal foil is provided with a catalyst cavity 56 and an indicator cavity 58. The bottom of the catalyst cavity is cut to provide at least one opening (not shown). A flame arrestor 29 is secured to the flange surrounding the hole by any suitable means. An absorbent strip 60 capable of absorbing an indicator solution is placed in the indicator cavity 38.

Figure 11:
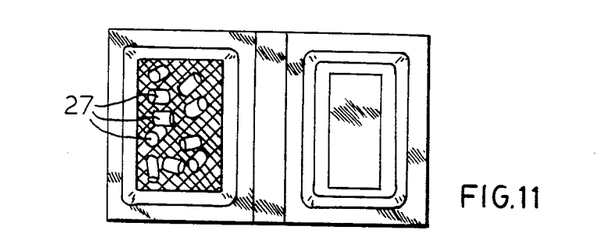
Figure 12:
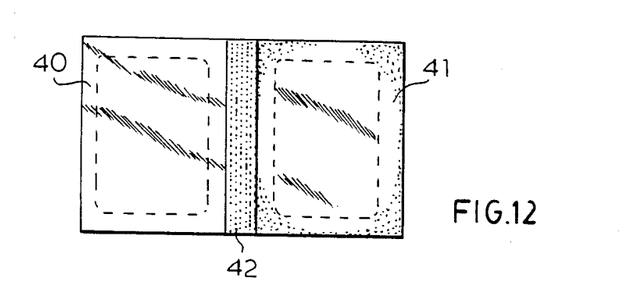

As shown in FIG. 11, catalyst pellets 27 are placed in the catalyst cavity 56. An indicator solution is absorbed into the strip 60. As shown in FIG. 12, a cover 40 of suitable material, such as metal foil, is securely affixed over the catalyst cavity 56. A peelable cover 41 is releasably affixed over the indicator cavity 58. An adhering means 42, such as double sided adhesive tape, is provided in the space between cover 40 and peelable cover 41.

Figure 13:
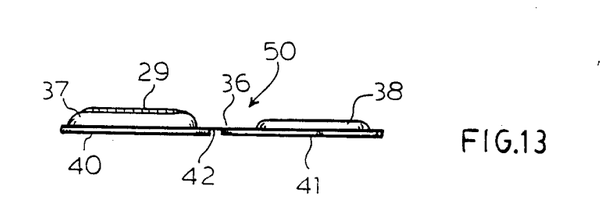
Figure 14:
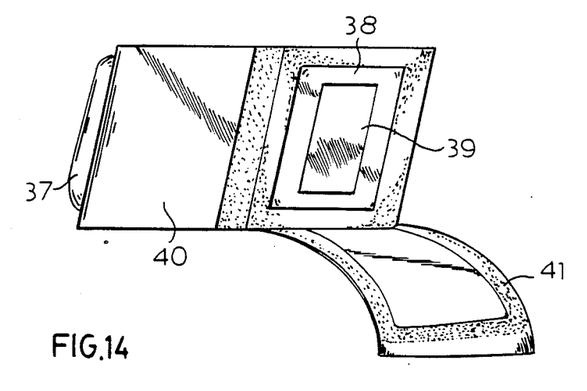
Figure 15:
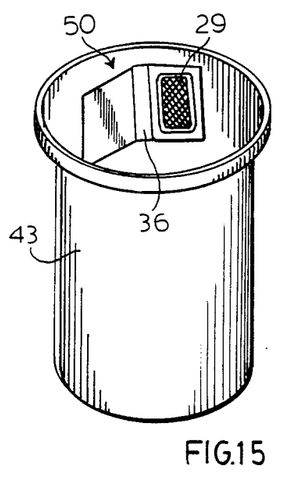
Figure 16:
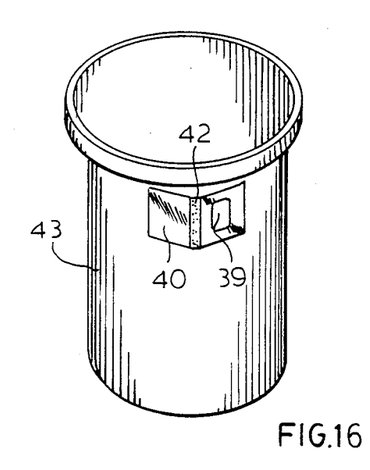

A top view of the completed catalyst and indicator envelope 50 is shown in FIG. 13. As shown in FIG. 14, the cover 41 is peeled away from surface surrounding the indicator cavity 58, when the envelope is placed in use. the adhering means 42 is then used to affix the envelope to the inside wall of an anaerobic jar 43 as shown in FIG. 15 and 16. This exposes the catalyst to reaction with oxygen and hydrogen through the opening in the flame arrestor 29. The hydrogen is generated by a separate hydrogen generating means (not shown) after the jar 43 is sealed. As shown in FIG. 16, the indicator strip 60 is easily visible from outside the jar.

For the embodiment of the invention wherein it is desired to provide an atmosphere having a predetermined level of carbon dioxide, a carbon dioxide generating composition if provided. The carbon dioxide generating composition includes a water soluble solid acid and a water soluble carbonate in amounts suitable for generating carbon dioxide and also for providing an acidic pH; in particular, a pH of less than 6 when dissolved in water. As representative examples of suitable acids, there may be mentioned: citric, tartaric, ascorbic, succinic, malic, fumaric, lactic acids and the like. As representative examples of suitable carbonates, there may be mentioned; sodium bicarbonate, sodium carbonate, potassium carbonate, sodium sesquicarbonate, etc. The preferred composition includes citric acid and sodium bicarbonate. The composition is preferably employed in the form of a tablet in which suitable lubricants and binders are generally also employed. It is, however, to be understood that forms other than a tablet may be used. The selection of suitable amounts to provide the desired carbon dioxide concentration for culturing and the acidic pH is deemed to be within the scope of those skilled in the art from the teachings herein.

In accordance with a particularly preferred embodiment, an oxygen indicator is also applied to the exterior of package 10. Such an indicator may be coated or otherwise applied to the metallic foil, and such indicator, as particularly shown in FIG. 1 is in the form of three different indicators, 18, 19 and 21. The indicators may be of methylene blue, resazurin, and indigo carmine which respond to different levels of oxygen, or which have different oxidation-reduction potentials. The use of such indicators will indicate different levels of oxygen. A similar indicator for monitoring the level of carbon dioxide may also be applied to the external surface of the metallic foil and is generally indicated as 23. Although such indicators have been particularly shown as being printed as spots on the exterior of the package, it is to be understood that the indicator may take other forms such as lettering of other designs.

As should be apparent, the package, in one embodiment, forms an integral unit for providing a microaerophilic or anaerobic atmosphere in that the package includes the materials for generating hydrogen and carbon dioxide, as well as the catalyst for catalyzing the reaction between hydrogen and oxygen and the indicators for indicating oxygen concentration and carbon dioxide concentration.

In employing the gas generating device of the present invention, the releasable cover, if used, is removed from the outside of the compartment 31. The liquid receiving compartment 11 is opened by cutting away or tearing a corner of the envelope 10 along a tear line, generally indicated as 22. A material capable of interacting with the gas generating materials in compartment 12, such as water, is introduced into compartment 11, and such water flows into compartment 12, preferably at a predetermined controlled volume and rate, and preferably through the wick 15. Upon contact with water, the tablets 13 and 14 generate hydrogen and carbon dioxide, which flow from compartment 12 into compartment 11 through the wick 15 and/or through the open gap 25 and ultimately into the container in which the envelope has been placed. The hydrogen reacts with oxygen in such container, with such reaction being catalyzed by the catalyst 27 in catalyst compartment 31 or catalyst unit 39. In addition, oxygen levels are indicated by means of the indicators 18, 19 and 21 which are applied to the exterior of package 10. Carbon dioxide concentration is indicated by indicator 23 which is also applied to the exterior of the package.

The invention will now be further described in the following examples, however, the scope of the invention is not to be limited thereby.

EXAMPLE 1

The following exemplifies a formulation to produce a microaerophilic atmosphere in accordance with the present invention, which includes a carbon dioxide generating tablet, a hydrogen generating tablet, a catalyst for the reaction between hydrogen and oxygen and oxygen indicators and carbon dioxide indicators applied to the exterior of the package. The package in accordance with the example is employed as a gas generator, with such gas generation being effected by the addition of 10 ml of water to the liquid receiving compartment.

| CARBON DIOXIDE GENERATING TABLET | |
|---|---|
| Citric Acid | 1.850 gm |
| Sodium Bicarbonate | 0.960 gm |
| In addition, the tablet includes | |
| suitable binder and lubricant; | |
| e.g., 0.1271 g talc and 0.531 g | |
| microcrystalline cellulose | |
| HYDROGEN GENERATING TABLET | |
| Sodium Borohydride | .27 gm |
| The tablet includes suitable binder | |
| and lubricants. The tablet can be | |
| coated with a water soluble gelatin | |
| to prevent decomposition | |
| CATALYST | |
| 1.2 g of 5% palladium on carbon catalyst | |
| FORMULATION OF INDICATOR BASE | |
| 18 g fructose | |
| 1.53 g $K_2HPO_4$ | |
| 0.35 g NaOH | |
| 2.5 mg phenyl mercuric nitrate | |
| FORMULATION OF METHYLENE BLUE INDICATOR | |
| Indicator Mixture | |
| 1.2 g indicator base | |
| 5 mg methylene blue | |
| Weight 1.2 g of dry indicator mixture with | |
| 0.333 g Gum of Tragacanth. Add 40 ml of | |
| water and boil. Cool, ready for use. | |
| FORMULATION OF INDIGO CARMINE INDICATOR | |
| Indicator Mixture | |
| 1.2 g Indicator base | |
| 5 mg indigo carmine | |
| Weight 1.2 g of dry indicator mixture | |
| with 0.3425 g Gum of Tragacanth. | |
| Mix with 40 ml of water and boil. | |
| Cool, ready to use. | |
| FORMULATION OF RESAZURIN INDICATOR | |
| Indicator Mixture | |
| 1.2 g Indicator base | |
| 5 mg of resazurin | |
| Weight 1.2 g of dry indicator mixture | |
| with 0.3345 g Gum of Tragacanth. | |
| Add 40 ml of water and boil. Cool, | |
| ready for use. | |
| FORMULATION OF CARBON DIOXIDE INDICATOR | |
| Sodium Bicarbonate | 0.02 g |
| Bromo Thymol Blue | 0.001 g |
| Gum of Tragacanth | 0.333 g |
| Mix with 40.0 ml of water and | |
| boil. Cool, ready for use. | |

EXAMPLE 2

In order to produce an anaerobic atmosphere in accordance with the present invention, Example 1 is repeated exactly except the hydrogen generating tablet includes 0.9 gm. of sodium borohydride.

EXAMPLE 3

PREPARATION OF PACKAGE

Two panels of aluminum foil measuring 5.9 inches by 3.3 inches were coated on one surface each with a vinyl laminate. One of the panels has a circular cavity about ¼ inch deep and about 1 inch in diameter in the position shown by reference numeral 31 of FIG. 1. A single hole about ⅜ inch in diameter was punched in the bottom of the cavity. A circular piece of 200 mesh fiberglass cloth one inch in diameter was sealed in the cavity over the hole and catalyst pellets were placed on the fiberglass cloth. A 1.5 inch square of aluminum foil was placed over the cavity and heat sealed to the panel bottom portion by a heat sealing apparatus.

Hydrogen and carbon dioxide generating tablets and a rectangle of Whatman #4 filter paper measuring 3 inches by 1.2 inches were placed on the laminated surface of the bottom panel in the positions shown in FIG. 2. The two panels were mated with the laminated surfaces facing each other and were inserted into a heat sealing apparatus having mating platens in the configuration shown in shaded outline in FIG. 1. The platens were closed and the apparatus was activated to provide a pressure of 70±40 psig for 2-3 seconds and at a temperature of 250-325 F. A second cover was then releasably sealed over the hole on the exterior side of the envelope.

The indicators were applied to the exterior of the package as follows:

Methylene blue—Apply 1 drop (0.05 cc.) of indicator to exterior aluminum surface of package and dry.

Indigo carmine—Apply 1 drop (0.05 cc.) of indicator to exterior aluminum surface of package and dry.

Resazurin—Apply 1 drop (0.05 cc.) of indicator to exterior aluminum surface of package and dry.

Although the invention has been described with respect to preferred embodiments thereof, it is to be understood that numerous modifications are possible within the scope of the invention. Thus, for example, a liquid other than water could be employed for generating the gas, and materials other than those particularly described could also be employed for generating gas. Thus, for example, a tablet capable of generating acetylene could be employed instead of a hydrogen generating tablet. Similarly, the tablet could be formulated for producing hydrogen in a manner other than as particularly described, e.g., hydrogen could be generated by another liquid, such as an acid; in particular, hydrochloric acid, although the use of water is preferred. Similarly, the liquid for generating the gas upon contacting the tablet could be within the package in a separate compartment or ampoule. Thus, the present invention is not limited to the particularly described embodiments, and numerous modifications and variations of the present invention are possible in light of the above teachings and, therefore, within the scope of the appended claims.

What is claimed is:

1. A package for removing oxygen from a gaseous mixture comprising:
   (a) a sealed envelope;
   (b) a first compartment within said envelope containing material for generating hydrogen;
   (c) a second liquid receiving compartment within said envelope in fluid and gas communication with said first compartment by means of a channel connecting said first and second compartments;
   (d) a catalyst unit affixed to the exterior of said envelope, said unit comprising a flame arrestor, a catalyst positioned on the surface of said flame arrestor and a backing material positioned over said catalyst and sealably engaged with said flame arrestor; and
   (e) adhering means between said unit and the exterior of said envelope.

2. The package in accordance with claim 1 wherein said envelope is metallic foil.

3. The package in accordance with claim 1 further comprising material in said first compartment, which, when contacted with water, generates carbon dioxide.

4. The package in accordance with claim 1 further comprising an indicator applied to the exterior of said package for determining the level of oxygen exterior to said package.

5. The package in accordance with claim 1 further comprising an indicator applied to the exterior of said package for determining the level of carbon dioxide exterior to said package.

6. The package in accordance with claim 1 wherein said flash arrestor is a porous thermostable material.

7. The package in accordance with claim 6 wherein said material is selected from the group consisting of fiberglass cloth, perforated metal and metal screen.

8. The package in accordance with claim 1 wherein said catalyst is selected from the group consisting of palladium, platinum, rhodium, ruthenium or iridium.

9. The package in accordance with claim 8 wherein said catalyst is supported on an inert carrier selected from the group consisting of alumina, carbon, fiberglass cloth, synthetic polymer and glass tape.

10. The package in accordance with claim 1 wherein said hydrogen generating material is sodium borohydride.

11. The package in accordance with claim 10 wherein the quantity of said sodium borohydride is from about 0.15 g to about 0.9 g.

12. The package in accordance with claim 1 further including means for controlling the flow of fluid through said channel at a predetermined rate.

13. The package in accordance with claim 12 wherein said flow controlling means is filter paper.

14. The package in accordance with claim 1 wherein said adhering means is between said backing material and said exterior.

15. A package for removing oxygen from a gaseous mixture comprising:
   (a) a sealed envelope;
   (b) a first compartment within said envelope containing material for generating hydrogen;
   (c) a second liquid receiving compartment within said envelope in fluid and gas communication with said first compartment;
   (d) a catalyst unit affixed to the exterior of said envelope, said unit comprising a flame arrestor and a catalyst positioned between said flame arrestor and said exterior; and
   (e) adhering means between said unit and the exterior of said envelope.

16. A package for removing oxygen from a gaseous mixture comprising:
   (a) a sealed envelope having top and bottom panels sealed together around their edges;
   (b) a first compartment within said envelope containing materials for generating hydrogen and carbon dioxide when contacted with water;
   (c) a second water receiving compartment within said envelope, said second compartment being in fluid and gas communication with said first compartment by means of a wick in a channel connecting said first and second compartments;
   (d) a catalyst unit affixed to the exterior of said envelope and under said second compartment, said unit comprising a flame arrestor, a catalyst positioned on the surface of said flame arrestor and a backing material positioned over said catalyst and sealably engaged with said flame arrestor; and
   (e) adhering means between said unit and the exterior of said envelope.

17. The package of claim 16 further comprising an indicator applied to the exterior of said envelope for determining the level of oxygen exterior to said package.

18. The package of claim 16 further comprising an indicator applied to the exterior of said envelope for determining the level of carbon dioxide exterior to said package.

19. The package in accordance with claim 16 further comprising a cavity in said bottom panel.

20. The package of claim 19 wherein said catalyst unit is positioned within said cavity and said flame arrestor is substantially flush with said bottom panel.

* * * * *